(12) United States Patent
Sigg et al.

(10) Patent No.: US 8,790,295 B1
(45) Date of Patent: Jul. 29, 2014

(54) PRESSURE MONITORING TO CONTROL DELIVERY OF THERAPEUTIC AGENT

(75) Inventors: Daniel C. Sigg, St. Paul, MN (US); Prasanga Hiniduma-Lokuge, Minneapolis, MN (US); Mary Morris, Mounds View, MN (US); Mike Ujhelyi, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 567 days.

(21) Appl. No.: 12/651,700

(22) Filed: Jan. 4, 2010

Related U.S. Application Data

(60) Provisional application No. 61/142,497, filed on Jan. 5, 2009.

(51) Int. Cl.
*A61M 31/00* (2006.01)

(52) U.S. Cl.
USPC ............................................. 604/67

(58) Field of Classification Search
USPC ................ 604/65–67, 503, 505, 890.1, 891.1
See application file for complete search history.

(56) References Cited

U.S. PATENT DOCUMENTS

| | | | |
|---|---|---|---|
| 4,657,536 A | 4/1987 | Dorman | |
| 4,791,931 A | 12/1988 | Slate | |
| 5,003,976 A | 4/1991 | Alt | |
| 5,368,040 A | 11/1994 | Carney | |
| 5,535,752 A | 7/1996 | Halperin | |
| 5,564,434 A | 10/1996 | Halperin | |
| 5,752,977 A | 5/1998 | Grevious | |
| 5,904,708 A | 5/1999 | Goedeke | |
| 6,480,745 B2 | 11/2002 | Nelson | |
| 6,622,050 B2 | 9/2003 | Thompson | |
| 7,235,067 B2 | 6/2007 | Morris | |
| 7,320,676 B2 | 1/2008 | Miesel | |
| 7,386,346 B2 | 6/2008 | Struble | |
| 2001/0041870 A1* | 11/2001 | Gillis et al. | 604/164.09 |
| 2005/0043675 A1 | 2/2005 | Pastore | |
| 2005/0075624 A1* | 4/2005 | Miesel | 604/505 |
| 2006/0074404 A1 | 4/2006 | Struble | |
| 2006/0111754 A1 | 5/2006 | Rezai | |
| 2006/0167359 A1 | 7/2006 | Bennett | |
| 2008/0243074 A1 | 10/2008 | Miesel | |

\* cited by examiner

Primary Examiner — Kami A Bosworth
(74) Attorney, Agent, or Firm — Carol F. Barry

(57) ABSTRACT

A method for adjusting delivery of a therapeutic fluid to a patient suffering from or at risk of pulmonary arterial hypertension includes introducing the therapeutic fluid to a patient via a catheter at a predetermined rate. The catheter is positioned to deliver the fluid to the right ventricle or the pulmonary artery. The catheter a one-way valve configured to allow the fluid to flow from the catheter to the target location. The method further includes monitoring pressure of the target location by monitoring internal catheter pressure, and adjusting the rate at which the therapeutic fluid is introduced to the catheter based on the monitored pressure. The rate at which the fluid is introduced to the catheter is increased if internal catheter pressure increases, and the rate at which the fluid is introduced to the catheter is decreased if the internal catheter pressure decreases.

3 Claims, 12 Drawing Sheets

PRESSURE MONITORING TO CONTROL DELIVERY OF THERAPEUTIC AGENT

FIELD OF THE INVENTION

The present disclosure related to implantable infusion devices; and more particularly, to use of such devices for treating pulmonary arterial hypertension using indirect or direct measurements of pulmonary arterial pressure as feedback to control delivery of therapy.

BACKGROUND OF THE INVENTION

Pulmonary arterial hypertension (PAH) is a progressive disease, eventually leading to right heart failure and death, with symptoms and mortality comparable to heart failure. There are two main types of PAH; primary PAH and secondary PAH. Primary PAH is of unknown etiology and is thought to be genetic in nature. Secondary PAH arises from known causes and can be associated with exposure to toxins, use of appetite suppressants or effects from diseases such as congenital heart disease, HIV, scleroderma, sickle cell disease and chronic liver disease. The estimated prevalence of PAH in 2007 in Europe, the U.S., and Japan is about 146,000.

In general, PAH results from narrowing or constriction of the pulmonary artery lumen, which results in increased pulmonary vascular resistance and increased pulmonary arterial pressures. This can also lead to increased afterload to the right ventricle, decreased cardiac output, increased right ventricle pressure and increased right ventricle size, ultimately leading to right ventricular failure. In patients with PAH, pressure in the right ventricle and pulmonary artery can be markedly increased relative to healthy individuals without PAH. For example, systolic pressure in the right ventricle may be about 75 mm Hg, while diastolic pressure tends to be only slightly elevated. Systolic pressure in the pulmonary artery may also be in about 75 mm Hg. Diastolic pulmonary arterial pressure may be around 30 mm Hg.

A number of therapeutic agents have shown some success in treating PAH. Such agents include, endothelin receptor antagonists, such as bosentan (TRACLEER®—Acetelion), phosphodiesterase type 5 inhibitors, such as sildenafil citrate (REVATIO®—Pfizer), and prostanoids, such as iloprost (VENTAVIS®—CoTherix/Schering AG), treprostinil sodium (REMODULIN®—United Therapeutics), and epoprostenol sodium (FLOLAN®—Glaxo SmithKline). Some of these drugs are formulated and approved for subcutaneous or intravenous administration and may be delivered subcutaneously or intravenously via external pump systems. While effective, such external systems can be cumbersome for the patient and can result in injection site pain.

To date, no fully implantable systems are used for delivering therapeutic agents for the treatment of PAH. However, such implantable systems have been used for treatment of a variety of diseases and often improve patient quality of life relative to chronic therapies that do not employ fully implantable systems. Such implantable systems typically include an implantable infusion device and a catheter coupled to the infusion device. One complication experienced with the use of implantable catheters is catheter occlusion resulting from blood ingression and blood clot formation in the catheter lumen. One solution proposed for preventing such occlusion is to incorporate a one-way valve, such as a one-way sleeve valve into a delivery region of a catheter to allow fluid to exit the lumen of the catheter into the body (but not from the body to the lumen). In addition and for purposes of catheter diagnostics, pressure monitors have been proposed that can monitor internal catheter pressure for purposes of diagnosing whether the catheter is obstructed; e.g. kinked or clogged, or contains a leak. However, the use of such pressure sensors for therapeutic purposes has not been described.

BRIEF SUMMARY OF THE INVENTION

The present disclosure describes methods, devices and systems useful for treating patients having pulmonary arterial hypertension (PAH) or other diseases in which internal body pressure provides an indication of disease state or status. The methods, systems and devices include implantable infusion devices and associated catheters.

In various embodiments, a method for monitoring pressure in a tissue is described. In the method, a catheter having a delivery region is operably coupled to an infusion device. The delivery region of the catheter has an opening for delivering therapeutic fluid from the infusion device to the tissue and has a one-way valve disposed in proximity to the opening. The one-way valve is configured to allow the therapeutic fluid to flow from the catheter through the opening to the tissue. The method includes infusing fluid from the infusion device through a lumen of the catheter at a predetermined rate, and monitoring pressure of the lumen of the catheter. The method further includes correlating a change in pressure of the lumen of the catheter with a change in pressure of the tissue or body fluid, wherein an increase in pressure of the lumen is correlated with an increase in pressure of the tissue or body fluid. In some embodiments, monitoring the pressure of the lumen of the catheter includes monitoring pressure of the therapeutic fluid within the infusion device. The pressure of the therapeutic fluid may be monitored by monitoring pressure in a tube through which the fluid flow, if the tube is in fluid communication with the catheter. A sensor disposed in the infusion device may be electronically coupled to electronics of the device for monitoring the pressure.

In various embodiments, a system is described. The system includes a catheter having a proximal end, a distal region including an opening, a lumen extending from the proximal end to the opening, and a one-way valve. The valve is disposed in proximity to the opening and is configured to allow fluid to exit the lumen through the opening. The system further includes an implantable infusion device having a housing, and a reservoir, an infusion mechanism, electronics and a pressure sensor disposed within the housing. The reservoir is configured to store therapeutic fluid. The infusion mechanism is configured to cause fluid from the reservoir to be infused through the lumen of the catheter when the catheter is operably coupled to the infusion device. The pressure sensor is configured and positioned such that the pressure sensor is capable of detecting pressure changes in the lumen of the catheter. The pressure sensor is operably coupled to the electronics. The electronics are configured to control the rate that the therapeutic fluid is delivered from the reservoir to the lumen of the catheter and are configured to modify the rate of delivery based on intralumenal pressure detected by the pressure sensor.

In various embodiments, a method for adjusting delivery of a therapeutic fluid to a patient suffering from or at risk of pulmonary arterial hypertension is described. The therapeutic fluid is delivered from an implanted catheter to a target region selected from the right ventricle or the pulmonary artery of the patient. The method includes introducing the therapeutic fluid to the catheter at a predetermined rate. The catheter has a delivery region implanted in the target location. The delivery region has a one-way valve configured to allow the fluid to flow from the catheter to the target location. The method further includes monitoring pressure of the target location by monitoring internal catheter pressure, and adjusting the rate at which the therapeutic fluid is introduced to the catheter based on the monitored pressure. The rate at which the fluid is introduced to the catheter is increased if internal catheter pressure increases, and the rate at which the fluid is introduced to the catheter is decreased if the internal catheter pressure decreases. In some embodiments, the delivery region of the catheter is implanted in the pulmonary artery. In some embodiments, the delivery region of the catheter is implanted in the right ventricle. Of course, the delivery region of the catheter may be implanted in any other suitable location, such as the superior vena cava. The therapeutic fluid may be delivered to the catheter via an implantable infusion device operably coupled to the catheter. In some embodiments, the implantable infusion device may include an access port in fluid communication with the catheter, and monitoring pressure of the catheter may include detecting pressure via the access port. In many embodiments, the internal catheter pressure is monitored via a pressure sensor disposed in the implantable infusion device.

In numerous embodiments, a system for delivering a therapeutic fluid to a patient suffering from or at risk of pulmonary arterial hypertension is described. The system includes a catheter having (i) a proximal end, (ii) a distal delivery region configured to be implanted in a right ventricle or pulmonary artery of a patient, and (iii) a lumen extending from the proximal end to the delivery region. The delivery region includes a one-way valve configured to allow fluid to flow from the lumen to outside the catheter. The system further includes an implantable infusion device operably couplable to the catheter. The infusion device includes a reservoir, an infusion mechanism, a pressure sensor, and electronics. The reservoir houses the therapeutic fluid. The infusion mechanism is configured to deliver the therapeutic fluid from the reservoir to the catheter. The pressure sensor is configured to measure internal pressure of the catheter when the catheter is operably coupled to the infusion device. The electronics are operably coupled to the pressure sensor and the infusion mechanism. The electronics are configured to compare internal fluid pressure of the catheter at first and second times and are configured to adjust flow rate of fluid delivered to the catheter via the infusion mechanism, such that the flow rate is increased if the internal pressure of the catheter is increased and flow rate is decreased if the internal pressure of the catheter is decreased.

In various embodiments, a method for adjusting delivery of a therapeutic fluid to a patient suffering from or at risk of pulmonary arterial hypertension is described. The therapeutic fluid is delivered from an implanted catheter via an implantable infusion device to the patient. The method includes introducing the therapeutic fluid to the catheter at a predetermined rate. The catheter has a delivery region implanted in the patient. The method further includes monitoring pressure of the pulmonary artery via a pressure monitor implanted in the patient, and adjusting the rate at which the therapeutic fluid is introduced to the catheter based on the monitored pressure. The rate at which the fluid is introduced to the catheter is increased if the monitored pressure increases, and the rate at which the fluid is introduced to the catheter is decreased if the monitored pressure decreases. In some embodiments, the pressure monitor is implanted and configured to monitor pressure in the right ventricle of the patient.

While information regarding monitored pressure may be employed in a closed-loop system, it will be understood that such information may be valuable in open-loop systems. For example, information regarding monitored pressure may be transmitted or otherwise provided to a physician, who may then determine, in their medical judgment, whether to adjust the dosage of therapeutic agent based on the pressure and other suitable factors.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION OF THE INVENTION

In the following detailed description, reference is made to the accompanying drawings that form a part hereof, and in which are shown by way of illustration several specific embodiments of devices, systems and methods. It is to be understood that other embodiments are contemplated and may be made without departing from the scope of spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As discussed above, the present disclosure relates generally to implantable infusion devices and to the use of such devices for treating diseases, such as pulmonary arterial hypertension, using indirect or direct measurements of pulmonary arterial pressure as feedback to control delivery of therapy. For the purposes of brevity and clarity, the present disclosure focuses on pulmonary arterial hypertension (PAH). However, it will be understood that the teachings presented herein may be readily applied to treatment of any disease in which pressure changes within the body provide an indication of disease state or status.

Any implantable infusion device suitable for implantation into a patient may be employed or modified according to the teachings presented herein. For example, infusion devices employing piston pumping mechanism, peristaltic pumping mechanisms, osmotic pumping mechanisms, electrochemical pumping mechanisms, or the like may be used. Preferably the pumps provide for variable or selectable rate infusion. One suitable implantable infusion device is the SYNCHROMED II® infusion device (Medtronic, Inc.).

Figure 1:
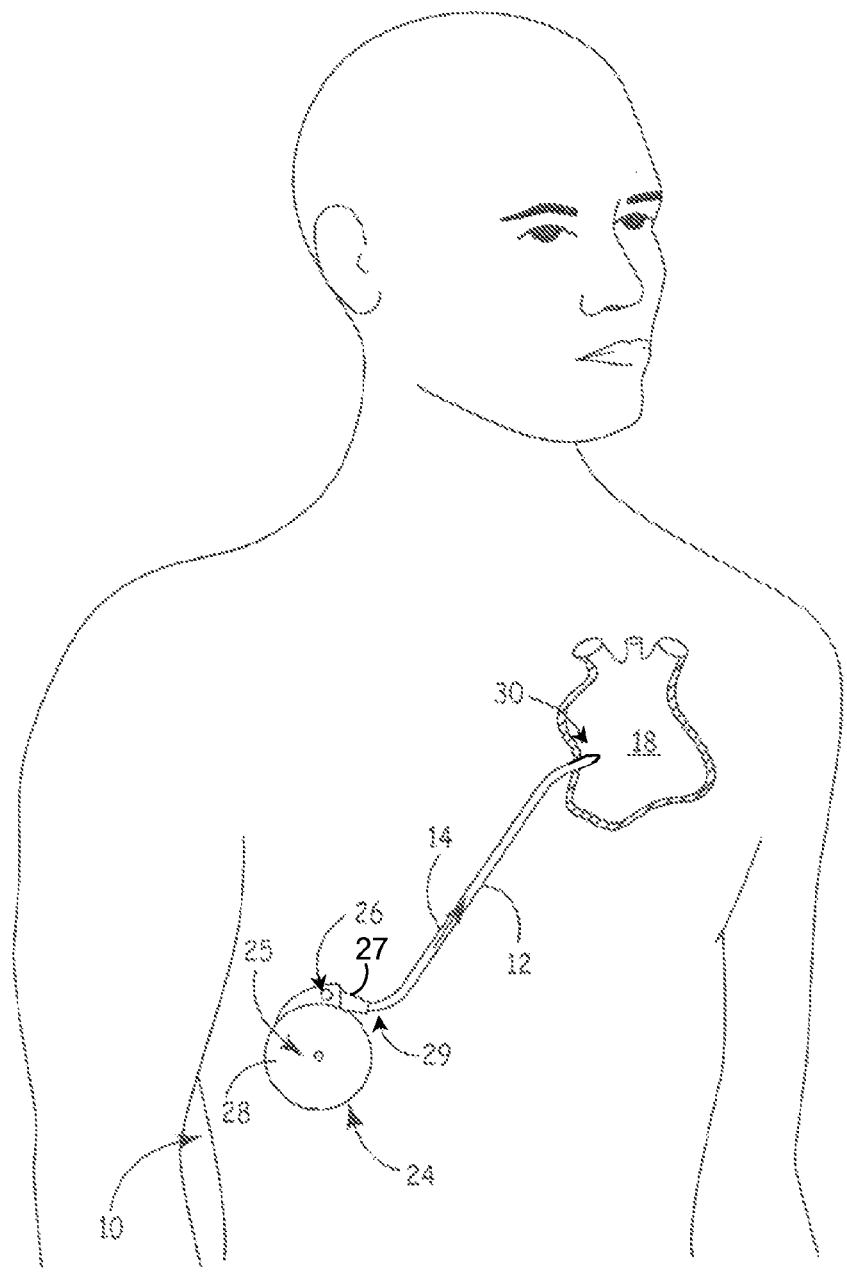
FIG. 1 shows an implantable infusion system implanted in a patient.

Referring now to FIG. 1 a representative implantable infusion device system 10 is shown implanted in a patient. The system 10 includes a catheter 12 and an infusion device 24. The infusion device 24 may be implanted in any suitable location of a patient; e.g. subcutaneously in the pectoral region or the abdomen. The depicted device 24 has a housing 28 encasing a reservoir, pumping mechanism, and electronics. A refill port 25 provides access to internal reservoir for filling or re-filling the reservoir with therapeutic fluid. A needle may be introduced into the access port 25 transcutaneously to infuse therapeutic fluid into the reservoir. The depicted infusion device 24 includes a connecter 27 for coupling the catheter 12 to the infusion device 24. The device 24 also includes a catheter access port 26 configured to be in fluid communication with the catheter 12 when the catheter 12 is coupled to the device 24. Fluid may be introduced to or withdrawn from the catheter 12 via the catheter access port 26.

Still with reference to FIG. 1, the catheter 12 has a body 14 that defines a lumen through which therapeutic fluid may flow. The catheter 12 has a proximal end 29 for coupling to the infusion device 24 and has a distal end 30. The distal region includes one or more openings for infusing therapeutic fluid from the lumen of the catheter 12 to a target location of the patient, which in the depicted embodiment is the heart 18. In various embodiments, a catheter 12 is positioned to deliver therapeutic fluid to various regions in proximity to the heart, which includes the heart itself. For example, the catheter 12 may be positioned to deliver therapeutic fluid directly to the superior vena cava, the right atrium, the right ventricle, the pulmonary artery, etc.

Figure 2:
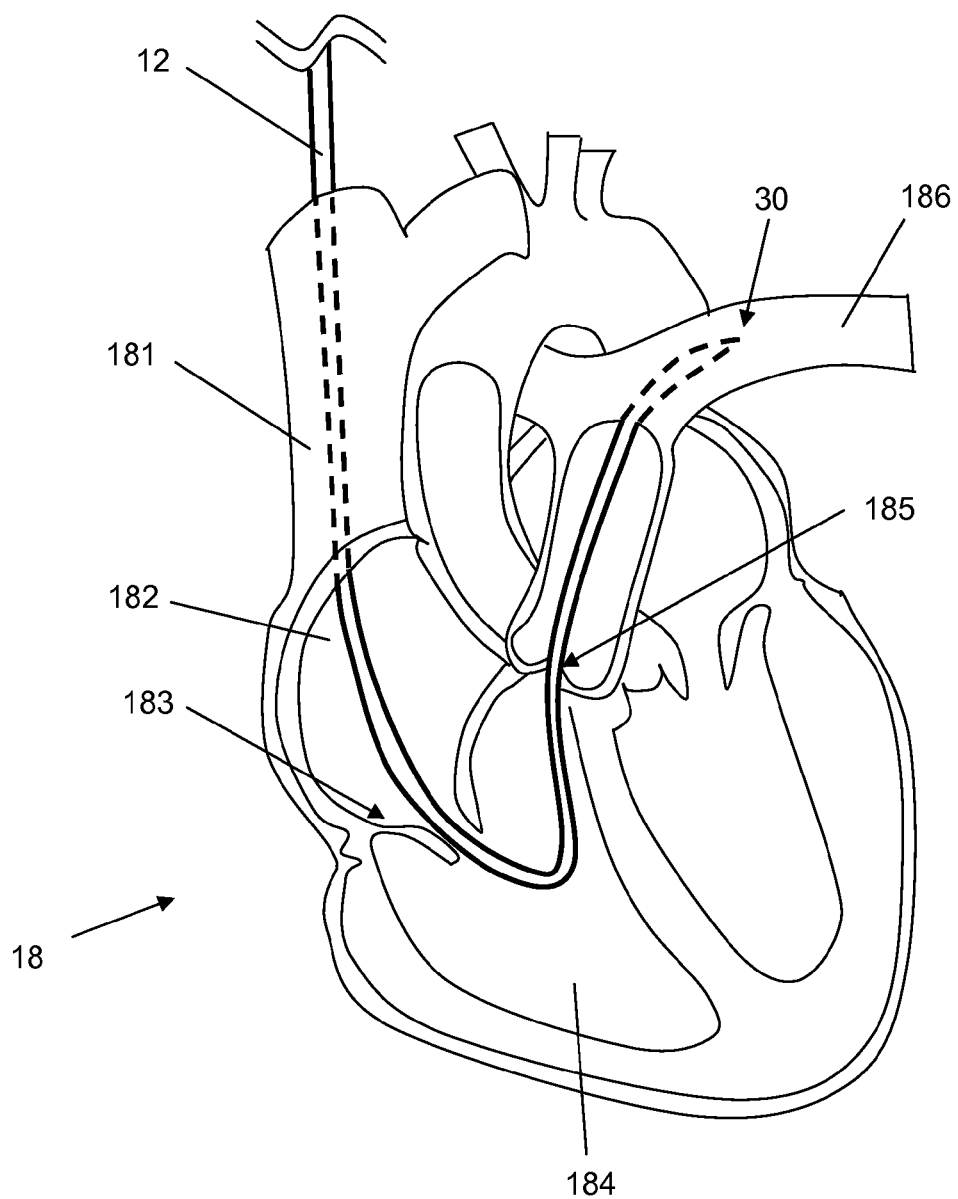
FIG. 2 shows a catheter fed through a heart into a pulmonary artery.

Referring now to FIG. 2, distal portion of catheter 12 is shown with distal end 30 implanted in the pulmonary artery 186. To get to the pulmonary artery 186, the distal end 30 of the catheter 12 is fed through the superior vena cava 181 into the right atrium 182, through the tricuspid valve 183, into the right ventricle 184 and past the pulmonary valve 185. Standard guide catheters, stylets or the like may be employed to navigate the catheter 12 through the heart 18. The catheter may include radiopaque markers or bands to facilitate location of the catheter as it is moved through the heart, with the assistance of standard navigation and visualization packages.

Figure 3:
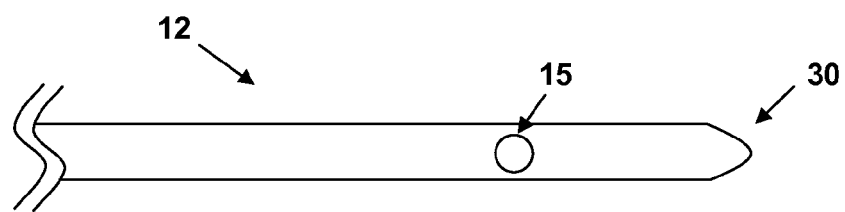
FIGS. 3-4 are schematic drawings of side views of distal portions of representative catheters.
Figure 4:
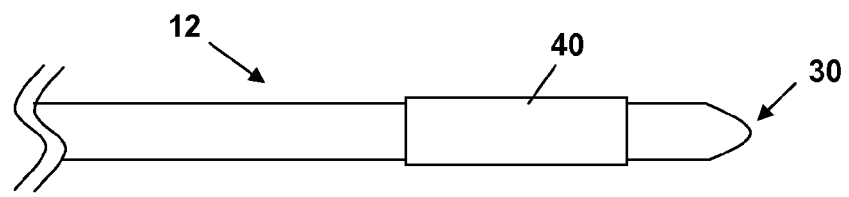

Any suitable catheter may be employed to introduce therapeutic fluid to a target region of a patient in accordance with the teachings herein. One example of a suitable catheter is Medtronic's Model 10642 central venous catheter. With reference to FIGS. 3-4, representative distal portions of catheters 12 are shown. In the depicted embodiments, the catheters 12 include one or more openings 15 in proximity to the distal ends 30 of the catheters 12. In the embodiment depicted in FIG. 4, the catheter 12 includes a one way sleeve valve 40 disposed about the opening. The one way sleeve valve 40 is configured to inhibit blood ingression into the opening 15 of the catheter 12 and to prevent blood clot formation in the lumen of the catheter 12. Of course any suitable one-way valve may be employed to prevent blood ingression. Examples of suitable one-way sleeve valves are described in Morris et al., Journal of Vascular Access, 2008, vol. 9, pp. 20-27 and in U.S. Pat. No. 7,235,067, which patent is incorporated herein by reference to the extent that it does not conflict with the present disclosure. Advantages of a sleeve valve are discussed in more detail below with regard to various embodiments. The opening 15 and one way valve or sleeve 40 may be positioned at any suitable location along the length of the catheter 12.

Figure 5:
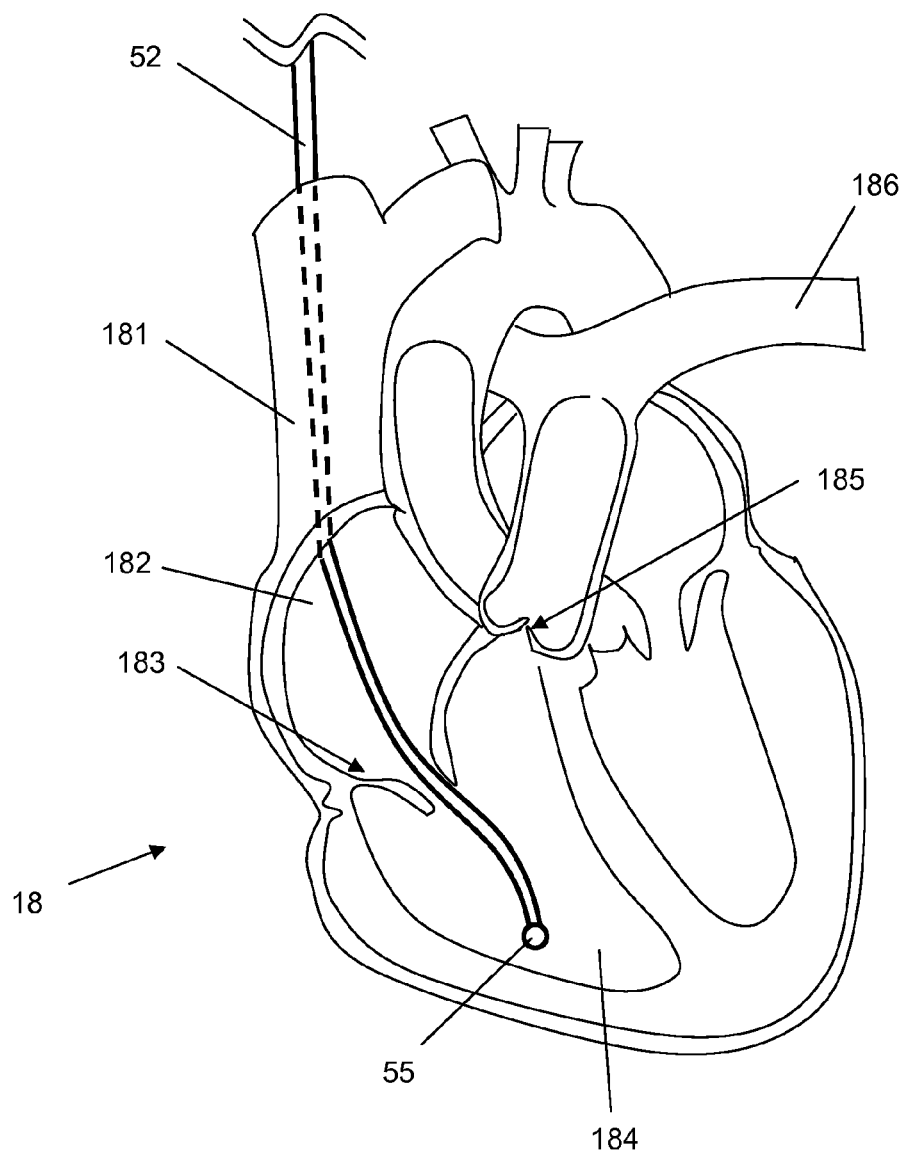
FIG. 5 shows a pressure sensor operably coupled to a lead positioned in a right ventricle.

Referring now to FIG. 5, a pressure sensor 55 is located in the right ventricle 184 of a heart 18. Pressure sensor 55 is located on the distal end of a medical lead 52, which may be operably coupled to a medical lead 52. The lead 52 may be operably coupled to a implantable monitoring device or to an infusion device that has pressure monitoring capabilities. One such monitoring device is the MEDTRONIC CHRONICLE® heart monitor. The lead 52 is inserted through the superior vena cava 181, the right atrium 182, past the tricuspid valve 183 and into the right ventricle 184. Of course, the pressure sensor 55 may be located in any suitable compartment of the heart 18. If the pressure sensor 55 is located in the right ventricle 184, the pressure of the right ventricle 184 can be directly measured or the diastolic pressure of the pulmonary artery may be estimated; e.g. as described in U.S. Pat. No. 7,386,346 to Chester Struble and assigned to Medtronic, Inc., which patent is hereby incorporated herein by reference to the extent that it does not conflict with the present disclosure. If the pressure sensor is located in the right atrium 182, the right artial pressure may be directly measured or the central venous pressure may be calculated; e.g. as described in U.S. Pat. No. 7,386,346. In various embodiments (not shown), the pressure sensor is located in the pulmonary artery.

Any suitable pressure sensor 55 may be employed according to the teachings presented herein. Examples of suitable pressure sensors are described in U.S. Pat. No. 7,320,676, issued on Jan. 22, 2008, assigned to Medtronic, Inc., and entitled "Pressure Sensing in Implantable Medical Devices".

Figure 6:
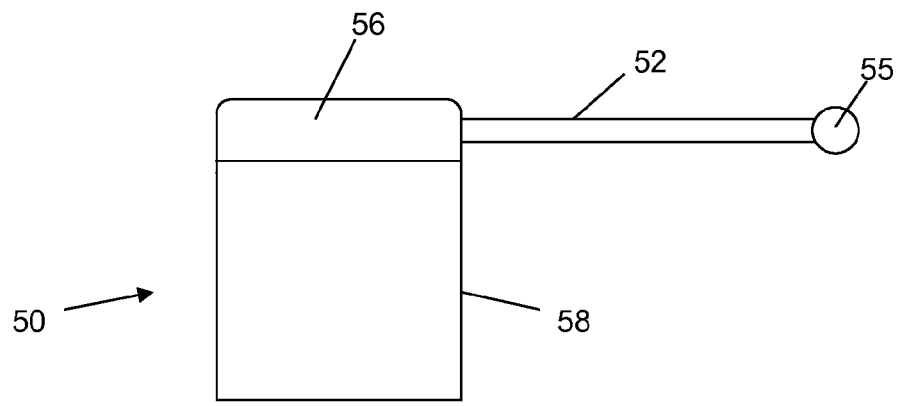
FIG. 6 is a schematic side view of a pressure monitoring system.
Figure 7:
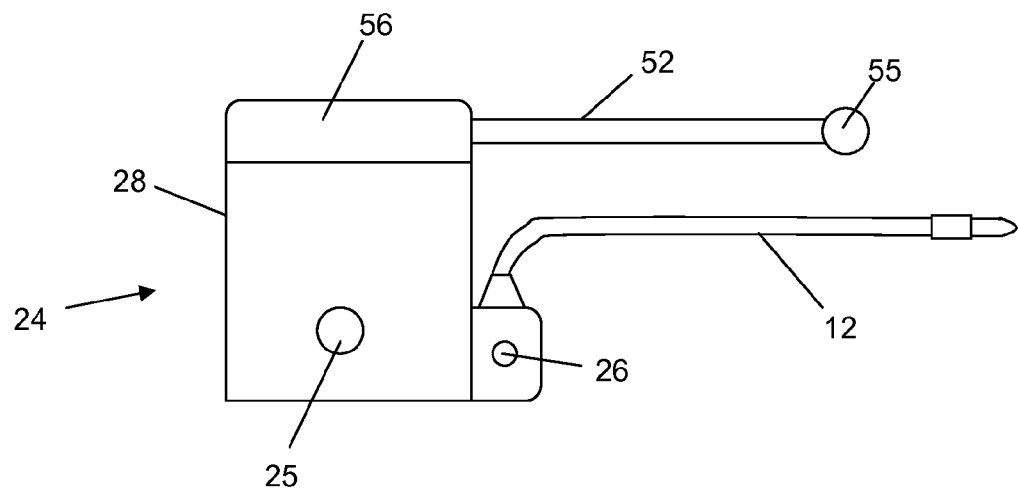
FIG. 7 is a schematic side view of an implantable infusion device with pressure monitoring capabilities.

Referring now to FIGS. 6-7, a pressure sensor 55 may be incorporated into a separate monitoring device 50 or into an infusion device 24 that has pressure monitoring capabilities. The pressure sensor(s) 55 are operably coupled to, and may be positioned at the distal end of, an implantable medical lead 52. The lead 52, and thus the pressure sensor 55, may be operably coupled to the device by insertion into a connector block 56 of the device. Typically the connector block 56 has a receptacle (not shown) for receiving the proximal end of the lead 52. A hermetically sealed feedthrough may be used to couple the lead 52 inserted into the connector block 56 to electronics of the device. In FIG. 6, the monitoring device 50 includes a hermetically sealed housing 58 in which electronics configured to monitor pressure are housed. In the embodiment depicted in FIG. 7, the infusion device 24 includes a hermetically sealed housing 28 in which electronics configured for monitoring pressure and controlling infusion are housed. In various embodiments, the electronics of the infusion device 24 may be configured to control infusion rate, etc. based on sensed pressure parameters in a closed-loop manner. The infusion device 24 may include a refill port 25 to provides access through the housing 28 to a reservoir; e.g., as described above with regard to FIG. 1. The infusion device 24 may also include a catheter access port 26 for infusing or withdrawing fluids via catheter 12.

Figure 8:
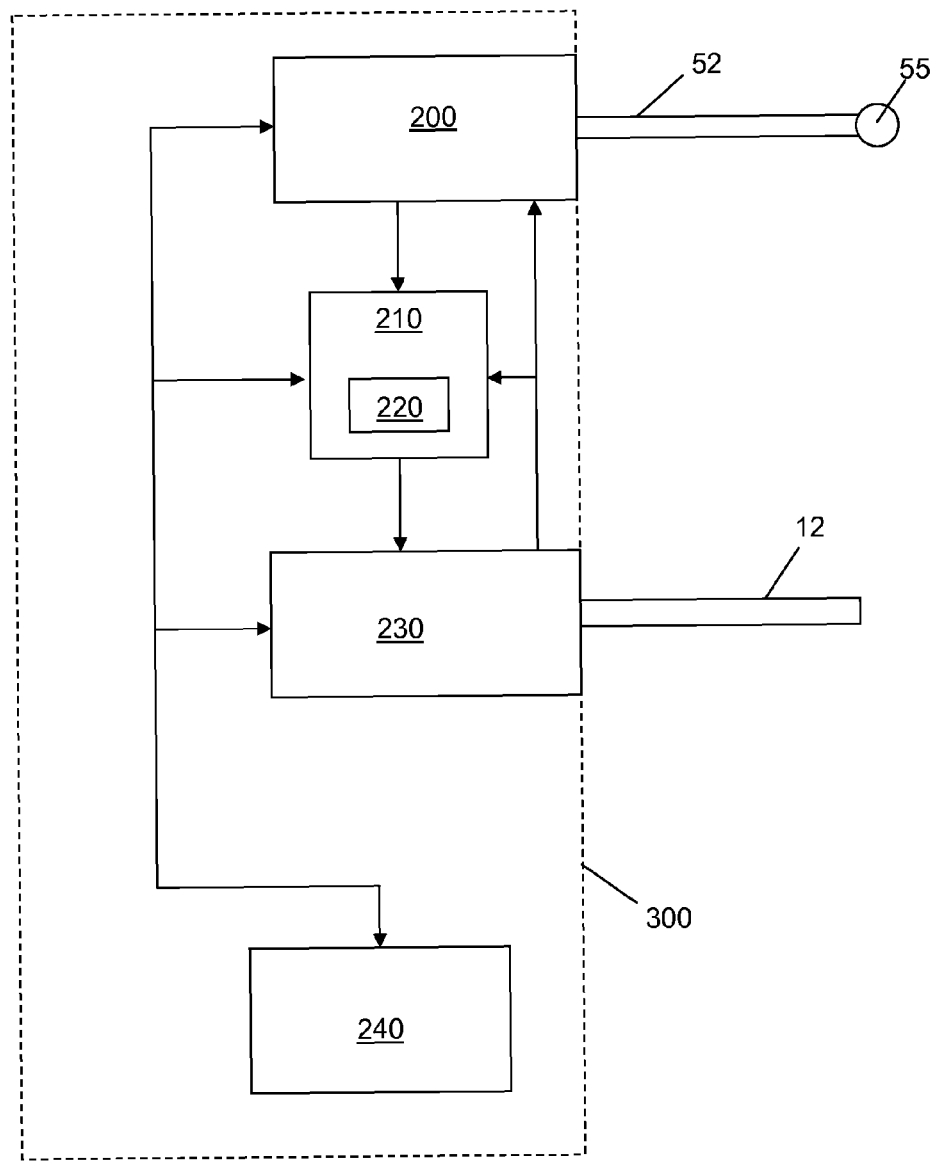
FIG. 8 is a schematic block diagram illustrating some components of an implantable infusion device with pressure monitoring capabilities.

With reference now to FIG. 8 some components of an infusion device capable of monitoring pressure are shown in block form. In the depicted embodiment, pressure sensor 55 sends information regarding pressure to the device electronics 300 of the device via lead 52. The depicted electronics 300 include a pressure sensor module 200 that may provide the information from sensor 55 to processor 210 or memory 220. The pressure sensor module 200 may convert the information prior to passage to processor 210 or memory 220. By way of example, the pressure sensor module 220 may include analog to digital converter circuitry, a multiplexor, filter, amplifier or the like. Any suitable electronic configuration and suitable arrangement of electrical components may be employed for handling information from pressure sensors. Information regarding sensed pressure may be stored in memory 220 and communicated to an external device via telemetry module 240. Information regarding sensed pressure may be used to control delivery of therapy; e.g. by sending instructions from processor 210 to therapy delivery module 230, which includes the infusion drive mechanism. The therapy instructions may be received from an external device in communication with the implanted device via telemetry module 240. Telemetry module 240 provides for wireless module provides for communication between the implantable device 24 and external device such as a programmer Communication may be bi-directional. Telemetry module 240 generally includes a telemetry antenna, a receiver, a transmitter 48, and a telemetry processor. Telemetry modules are generally known in the art and are further detailed in U.S. Pat. No. 5,752,977, entitled "Efficient High Data Rate Telemetry Format for Implanted Medical Device" issued to Grevious et al. (May 19, 1998).

It should be understood that only some selected electronic components are depicted in FIG. 8 and that electronics 300 may be configured in any suitable manner and may include any suitable components. For example, electronics 300 may include a clock, a power management module, a power source, a system reset module, a diagnostics module, or the like. It should also be understood that the pressure sensor module 200 may, in some respects, be considered to include processor 210 or memory 220, even though they are depicted as separate in FIG. 8.

Figure 9:
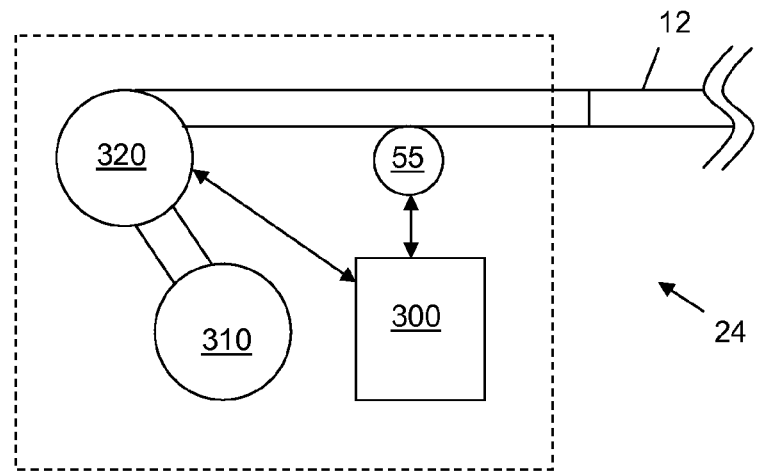
FIGS. 9-10 are schematic block diagrams illustrating some components of implantable infusion devices.
Figure 10:
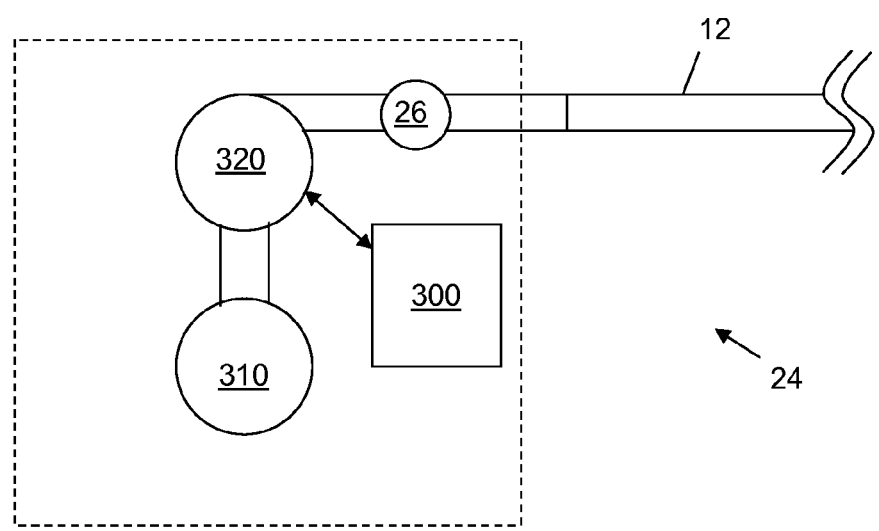

With reference to FIGS. 9-10, alternative embodiments for monitoring pressure are shown. In FIG. 9, the infusion device 24 includes a pressure sensor 55, which is positioned in the device 24 such that it will be in fluid communication with the lumen of the catheter 12 when the catheter 12 is operably coupled to the device 24. In FIG. 10, catheter access port 26 is shown as being in fluid communication with a catheter 12 operably coupled to the device 24. A pressure monitoring device with a pressure sensor may be inserted into the catheter access port 26 to measure pressure within the lumen of the catheter 12. Whether pressure in a lumen of the catheter 12 is measured via an external device through the catheter access port 26 or via a pressure sensor 55 disposed with the device 24, information regarding the sensed pressure may be used to alter delivery of therapeutic agent. For example, in the embodiment depicted in FIG. 9, pressure sensor 55 sends information to electronics 300 of the device 24, which can alter the rate of delivery of therapeutic agent via instructions sent to the drive mechanism 320 of the infusion device 320. The drive mechanism 320 may then draw fluid containing therapeutic agent at the instructed rate from reservoir 310 and deliver the fluid to the patient via the catheter 12. In the embodiments depicted in either of FIG. 9 or 10, information regarding the pressure may be sent or obtained by an external device. Instructions regarding infusion rate may be sent to electronics 300 via an external device, and electronics 300 can control rate of delivery via control over drive mechanism 320. It should be understood that in some embodiments (not shown), electronics may control components other than a drive mechanism, such as a valve or the like, to affect the delivery rate of therapeutic fluid. It should be further understood that the drive mechanism may be configured, in various embodiments, to push fluid from the reservoir (e.g., in devices employing a propellant) or may be the reservoir itself (e.g., elastomeric reservoir).'

Regardless of how pressure in a lumen of a catheter is measured, the pressure may be indicative of pressure of tissue into which the catheter is implanted, particularly with catheters employing a one-way valve at an opening in the delivery region of the catheter (see, e.g., FIGS. 3-4 and associated text). Preferably, all of the openings in the delivery region are valved. Assuming a constant rate of flow of fluid through a catheter having a single hole with a one-way sleeve valve, an increase (or decrease) in internal catheter pressure can correlate to an increase (or decrease) in physiological pressure at the implant site. Such an increase in internal catheter pressure relates to an increase in pressure needed to overcome increased external physiological pressure acting on the valve and inhibiting the valve from opening.

Using simple physics of a fluid column:

$$P_{catheter} = P_{implant\ site} + P_{flow\ rate} + P_{sleeve\ hoop\ strength} + P_{cracking\ pressure} \quad \text{(Equation 1)},$$

where $P_{catheter}$ is the pressure within the lumen of the catheter; $P_{implant\ site}$ is the physiological pressure at the site of implantation of the catheter; $P_{flow\ rate}$ is the pressure due to the flow of fluid and resistance through the catheter; $P_{sleeve\ hoop\ strength}$ is the pressure required to keep the elastic material of the sleeve valve open; $P_{cracking\ pressure}$ is the pressure required to open the valve.

Based on a derived or measured $P_{implant\ site}$ at the time of implant, a physician may program a specific flow rate or infusion rate profile for the infusion device. The pressure may be monitored at or for a time following the setting of the initial flow rate or profile. The pressure at the later time can be expressed as:

$$P_{catheter\_new} = P_{implant\ site\_new} + P_{flow\ rate\_initial} + P_{sleeve\ hoop\ strength} + P_{cracking\ pressure} \quad \text{(Equation 2)}.$$

For a given catheter of a given material, length, diameter, valve, etc. at a given flow rate and external pressure, $P_{flow\ rate}$, $P_{sleeve\ hoop\ strength}$, and $P_{cracking\ pressure}$ are known or can be readily determined empirically. Thus, if $P_{catheter\_new}$ is greater than $P_{catheter\ initial}$, $P_{implant\ site\_new}$ is greater than $P_{implant\ site\_initial}$. If the internal pressure of the catheter changes, a change in the rate or profile of infusion may be desired. Such a change in infusion parameters may be initiated by a physician following transmission of information regarding catheter pressure from the device to the physician; e.g. via an external programmer or network, or initiated by the device via programmed algorithms.

Figure 11:
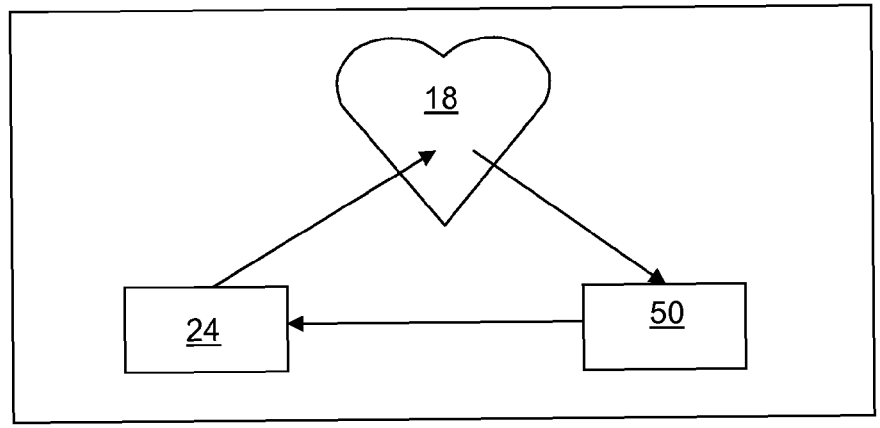
FIGS. 11-15 are schematic diagrams of various systems capable of infusing therapeutic fluid and monitoring pressure.
Figure 12:
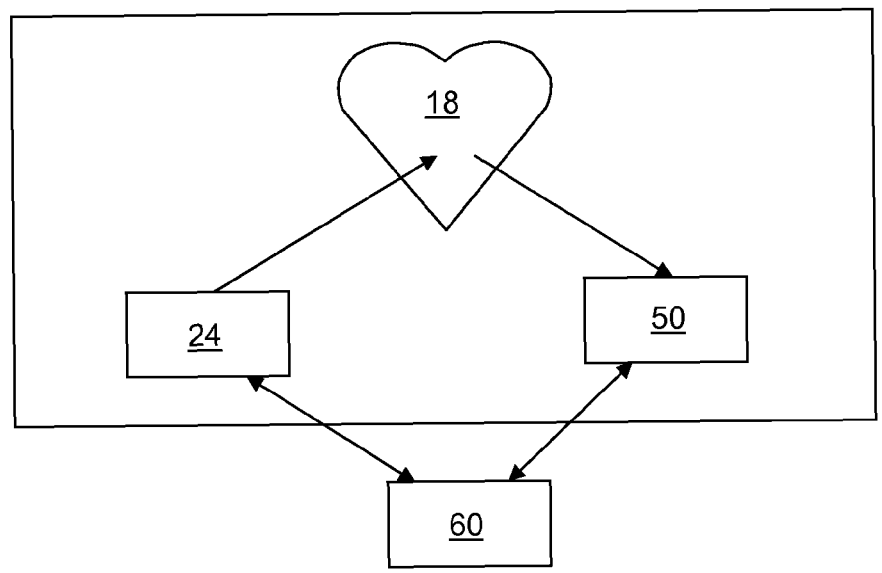

Referring now to FIGS. 11-14, various configurations of pressure monitor devices, infusion devices, infusion devices having pressure monitoring capabilities, and external devices are illustrated. As shown in FIGS. 11-12, a system may include separate implantable infusion devices 24 for infusing therapeutic fluid to the heart 18 and implantable monitoring device 50 for monitoring pressure in the heart 18 or associated veins or arteries. The infusion device 24 may communicate with the monitoring device 50 directly (FIG. 11) or via an external device 60 (FIG. 12). By way of example, the external device 60 may receive information regarding pressure from the monitor 50 and send instructions to the infusion device 24 regarding new infusion parameters. The infusion parameters may be input by a physician or other healthcare provider based on the pressure information. Direct communication of infusion device 50 with monitoring device 50 may be wireless or via a wire.

Figure 13:
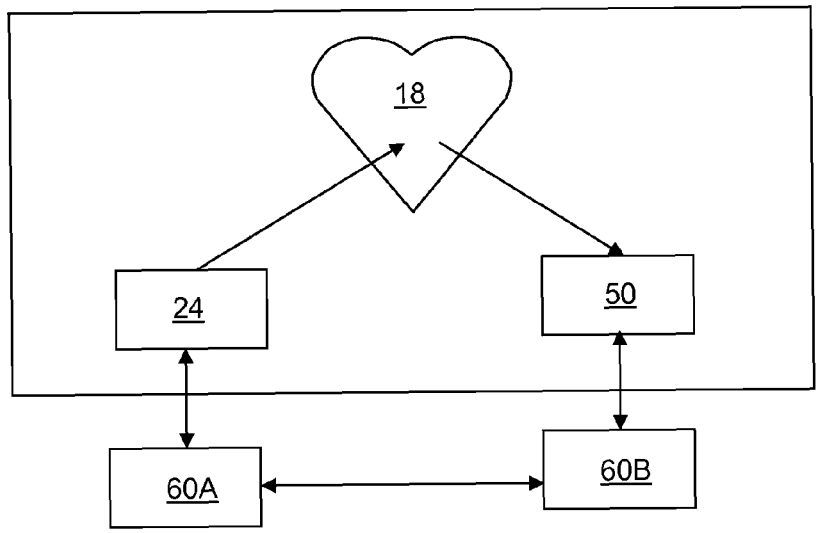
Figure 14:
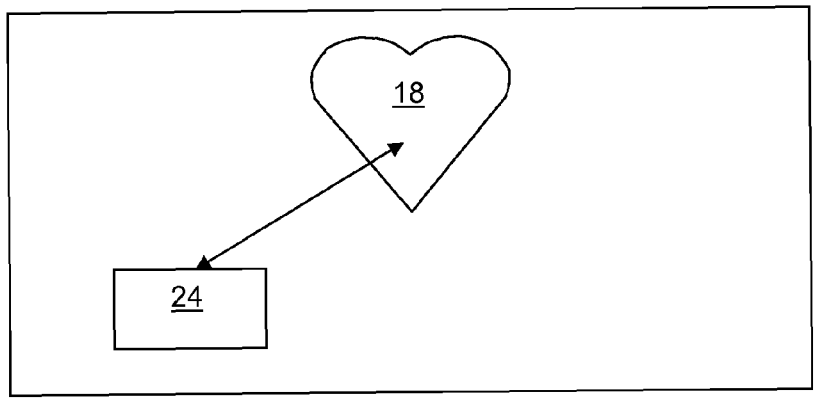

With reference to FIG. 13, infusion device 24 may communicate (e.g. receive instructions) with first external device 60A and monitor 50 may communicate (e.g. send information regarding pressure) with a second external device 60B. The first 60A and second 60B external devices may be in communication, e.g. wirelessly or via a network. Of course, a physician or other health care provider can view information received by the second external device 60B and input infusion parameters in to first external device 60A to be sent to infusion device 24. In the embodiment depicted in FIG. 14, the infusion device 24 has pressure monitoring capabilities. The infusion rate altered by the device 24 as pressure changes occur. Of course, the device 24 may include a telemetry module for communication with devices external to the patient.

Figure 15:
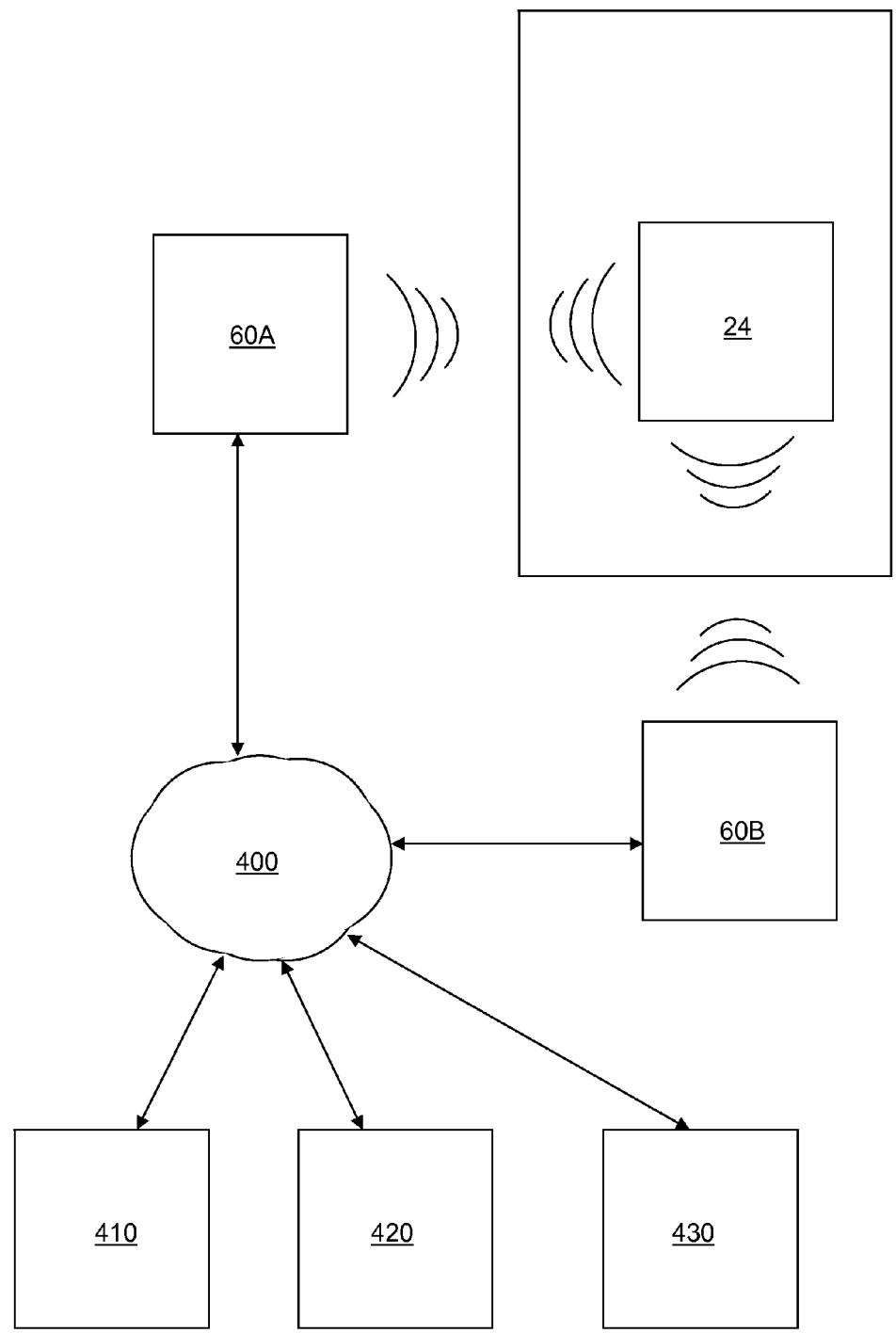

Referring now to FIG. 15, a system including a network 400 is shown. In the depicted system, an implantable medical device 24 is capable or wirelessly communicating with one or more external devices 60A, 60B. The external devices 60A, 60B capable of communicating with one or more additional devices 410, 420, 430 through the network 400. One or more intermediary devices (not shown) may be employed between the external devices 60A, 60B and the network 400 or the additional devices 410, 420, 430. One or more of the additional devices 410, 420, 430 may enable a physician in a clinic to remotely evaluate pressure changes and determine whether to remotely instruct the infusion device 24 to change infusion parameters. Examples of such remote networks for patient care associated with implantable medical devices include Medtronic Inc.'s CareLink system and those systems described in, for example, U.S. Pat. No. 5,752,976 to Duffin et al, issued on May 19, 1998, entitled "World Wide Patient Location and Data Telemetry System for Implantable Medical Devices" and assigned to Medtronic, Inc.; and U.S. Pat. No. 6,480,745 to Nelson et al., issued on Nov. 12, 2002, entitled "Information Network Interrogation of an Implanted Device" and assigned to Medtronic Inc., which patents are hereby incorporated herein by reference in their entirety to the extent that they do not conflict with the disclosure presented herein.

Figure 16:
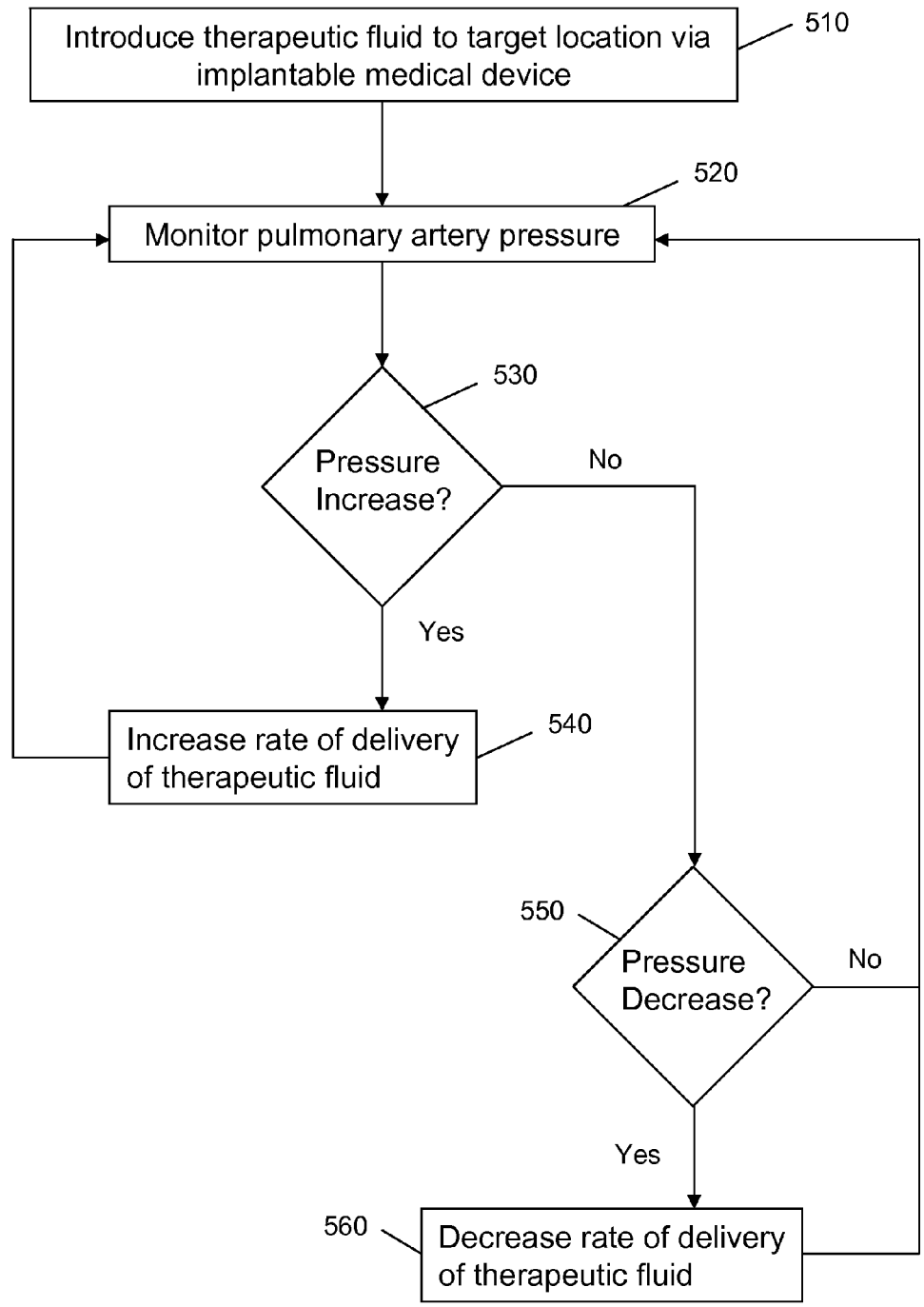
FIGS. 16-17 are schematic flow diagrams illustrating representative methods.
Figure 17:
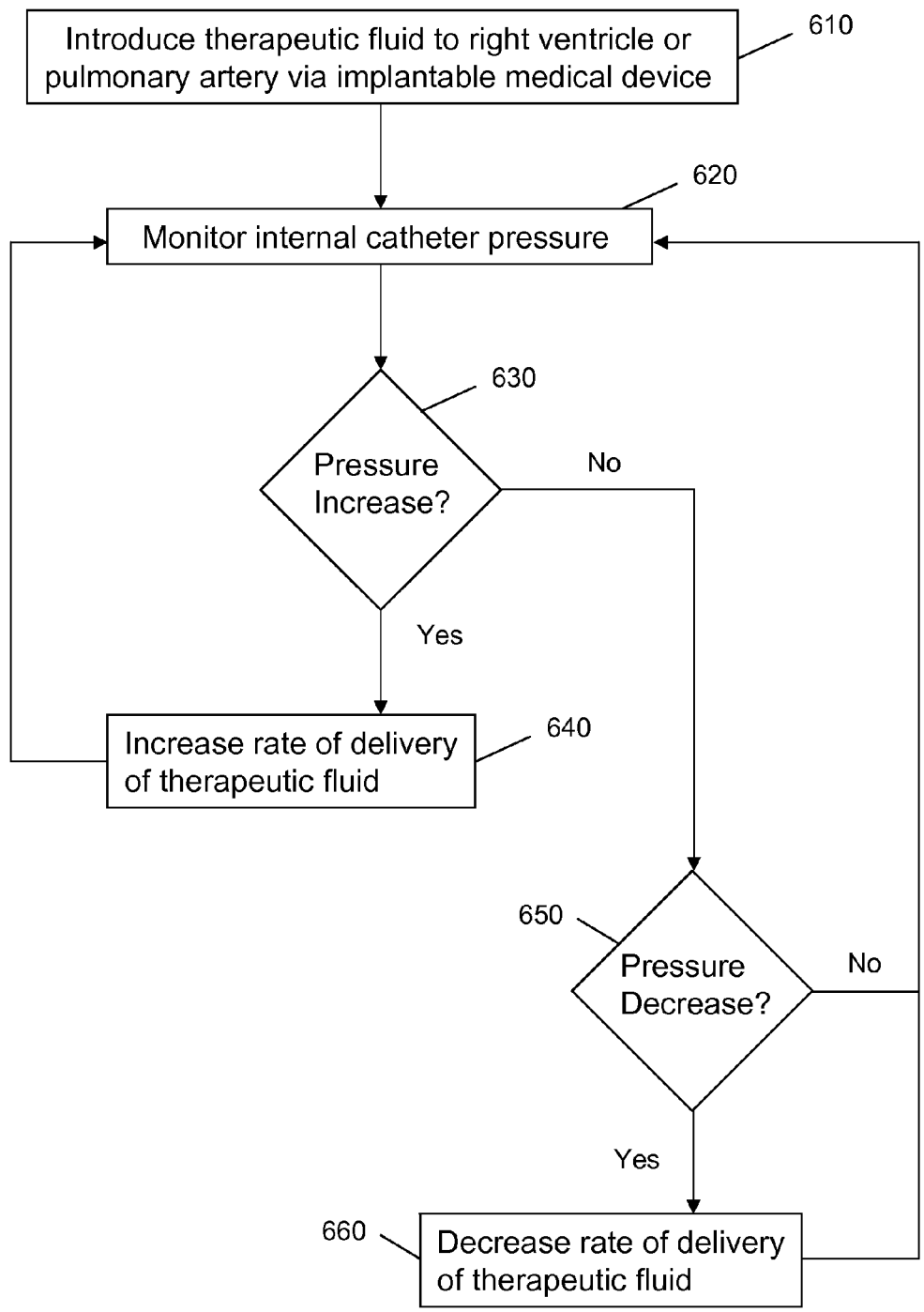

It will be understood that the components and configurations described with regard to FIGS. 1-15 are but examples of components and configurations of devices and systems that may be employed to carry out the methods described below. However, for the sake of convenience, the discussion that follows with regard to the method illustrated in the flow diagram of FIGS. 16-17 will refer to components and configurations as described with regard to FIGS. 1-15. It will be further understood that, while the method illustrated in FIGS. 16-17 is described with regard to pulmonary arterial hypertension (PAH), the concepts of the method may be employed with regard to any therapy in which physiological pressure changes warrant changes in fusion rate or profile of therapeutic agent delivered by an implantable medical device.

Prior to a discussion of the methods depicted in FIGS. 16-17, a brief discussion of the diagnosis of PAH and therapeutic agents useful for treating PAH is presented below.

Patients with PAH often present with one or more of breathlessness, fatigue, angina, syncope, peripheral edema and abdominal distension. Associated conditions may include connective tissue disease, congenital heart disease, HIV, and sickle cell disease. Diagnosis may be confirmed with ECG, chest X-ray, or Doppler echocardiogram. Pulmonary function tests and blood gas, high resolution computed tomography, and pulmonary angiography may be employed to identify other causes. Classification may verified by blood tests and immunology, HIV test, abdominal ultrasound, six-minute walk test and peak VO2, and right heart catheterization. Echocardiography may reveal enlarged right ventricles, decreased LV cavity size, abnormal septal configuration consistent with right ventricular overload, or marked dependence on atrial systole for ventricular filling. Chest X-ray may reveal evidence of cardiomegaly and enlarged pulmonary arteries. Right heart catheterization is currently employed to confirm and characterize PAH. PAH may be defined as a mean pulmonary arterial pressure of greater than 25 mm Hg at rest and greater than 30 mm Hg during exercise, with a pulmonary capillary wedge pressure of less than 15 mm Hg. Once a patient is diagnosed as suffering from or at risk of PAH, the patient may choose to have an infusion system implanted for chronic delivery of one or more therapeutic agents for treatment of PAH.

Systemic delivery of therapeutic agents is typically effective for treating PAH. Accordingly, therapeutic agents may be delivered by an implantable infusion device to nearly any location that results in systemic distribution of the therapeutic agent. For example, the therapeutic agent may be delivered subcutaneously, intravenously, intracardially, or the like. Any suitable agent for treating PAH may be delivered by an infusion device. For example, one or more of an endothelin receptor antagonist, a phosphodiesterase type 5 inhibitor, a prostanoid, or the like may be delivered. Bosentan is an example of a suitable endothelin receptor antagonist; sildenafil is an example of a suitable phosphodiesterase type 5 inhibitor; and iloprost, treprostinil, and epoprostenol are examples of suitable prostanoids that may be used for treatment of PAH. For infusion via an implantable infusion device, the therapeutic agent(s) is preferably formulated in an infusible form, such as a solution, suspension, dispersion, or the like.

Solutions, suspensions, or dispersions may be formulated according to techniques well-known in the art (see, for example, Remington's Pharmaceutical Sciences, Chapter 43, 14th Ed., Mack Publishing Co., Easton, Pa.), using suitable dispersing or wetting and suspending agents, such as sterile oils, including synthetic mono- or diglycerides, and fatty acids, including oleic acid, as needed. Solutions, suspensions or dispersions of therapeutic agents may be prepared in water, saline, isotonic saline, phosphate-buffered saline, citrate-buffered saline, and the like and may optionally mixed with a nontoxic surfactant. Dispersions may also be prepared in glycerol, liquid polyethylene, glycols, DNA, vegetable oils, triacetin, and the like and mixtures thereof. Under ordinary conditions of storage and use, these preparations may contain a preservative to prevent the growth of microorganisms. Pharmaceutical dosage forms suitable for injection or infusion include sterile, aqueous solutions, suspensions, or dispersions or sterile powders comprising an active ingredient which powders are adapted for the extemporaneous preparation of sterile injectable or infusible solutions or dispersions. Preferably, the ultimate dosage form is a sterile fluid and stable under the conditions of manufacture and storage. A liquid carrier or vehicle of the solution, suspension or dispersion may be a diluent or solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. Proper fluidity of solutions, suspensions or dispersions may be maintained, for example, by the formation of liposomes, by the maintenance of the desired particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption; for example, aluminum monosterate hydrogels and gelatin. Excipients that increase solubility, such as cyclodextrin, may be added.

Any suitable concentration of therapeutic agent may be present in an injectable composition according to various embodiments of the invention. Such concentrations may be based on concentrations required to deliver an effective amount of the therapeutic agent in a suitable volume. A fluid composition comprising one or more therapeutic agent for treating PAH may be delivered in any amount effective to treat PAH. Concentrations and effective amounts may be determined based on dosages of currently employed therapies, such as bosentan, sildenafil, iloprost, treprostinil, and epoprostenol, taking into account differences in route of administration. Reference to a particular therapeutic agent herein includes reference to a pharmaceutically acceptable, salt, hydrate or polymorph thereof.

Sterile injectable compositions may be prepared by incorporating one or more therapeutic agent in the desired amount in the appropriate diluent or solvent with various other ingredients as enumerated above and, as desired, followed by sterilization. Any means for sterilization may be used. For example, sterilization may be accomplished by heating, filtering, aseptic technique, and the like, or a combination thereof. In some circumstances it may be desirable to obtain a sterile powder for the preparation of sterile injectable solutions. Such sterile powders may be prepared by vacuum drying and freeze-drying techniques, which yield a powder of the active ingredient plus any additional desired ingredient present in a previously sterile-filtered solutions.

Referring now to the flow diagram depicted in FIG. 16, therapeutic fluid may be introduced into a target site of a patient (510). As indicated above, for treatment of PAH, the target location may be any suitable location. For example, therapeutic fluid may be administered to the superior vena cava, the right atrium, the right ventricle, the pulmonary artery, subcutaneously, or the like. Pulmonary artery pressure is monitored (520) either directly or indirectly. For example, a pressure sensor may be placed in the right ventricle for indirect measurement of pulmonary artery pressure or may be placed in the pulmonary artery for direct measurement. A determination may be made as to whether pulmonary arterial pressure has increased (530) and dosage or rate of infusion of therapeutic fluid may be increased (540). If the pressure has been determined to decrease (550), the dosage or rate of infusion of therapeutic fluid may be decreased (560). Following an increase or decrease in dosage, further monitoring or pulmonary arterial pressure (520) can be used to determine whether the altered rate of infusion was effective at bringing pressure into desired ranges.

By way of example, it may be desirable for additional therapeutic agent to be administered if pulmonary arterial pressure is greater than about 25 mm Hg at rest or greater than about 35 mm Hg during exercise; it may be desirable to decrease the rate of infusion of therapeutic clued if pulmonary arterial pressure is less than about 20 mm Hg at rest or less than about 25 mm Hg during exercise; and it may be desirable to maintain therapeutic dosage and infusion rate is pulmonary arterial pressure is about 22 mm Hg at rest or about 30 mm Hg during exercise. Activity and heart rate sensors, as generally known in the art, can be employed to determine whether the subject is at rest or exercising, and to what extent. It will be understood that pulmonary arterial pressure may be one of several factors that may be considered in determining whether to adjust dosage. By having information regarding pulmonary arterial pressure, a physician or other heath care provider will be better armed with relevant information for making dosage determinations.

The flow diagram in FIG. 17 is similar to that described with regard to FIG. 16. However, the flow diagram in FIG. 17 is directed to an embodiment where changes in pulmonary artery pressures are determined by changes in intracatheter pressure. In the depicted embodiment, therapeutic fluid for treating PAH is introduced into the right ventricle (RV) or pulmonary artery (PA) (610) via a catheter operably coupled to an implantable infusion device. The distal end of the catheter that includes a delivery region having one or more valved openings is implanted in the RV or PA. The internal pressure of the catheter is monitored (620), either directly or indirectly, e.g. as described above with regard to FIGS. 9-10. If the intracatheter pressure increases (630), the rate of delivery may be increased (640). If the intracatheter pressure decreases (650), the rate of delivery may be decreased (660).

With regard to the methods described with regard to FIGS. 16-17, it will be understood that an increase in delivery rate may be one or more bolus doses delivered on top of a continuous background infusion rate; may be an increase in infusion rate over a period of time, or the like. It will also be understood that the magnitude of the change in pressure may determine the magnitude in the change in infusion rate. For example, the larger the increase in pressure, the greater the increase in infusion rate. However, for any given therapeutic agent, there may be a dosage that should not be exceeded.

The principles of the methods, systems and devices described herein may be used for treating or monitoring aspects of diseases other than PAH. Treating or monitoring diseases other than PAH, in which internal body pressure provides an indication of disease state, is contemplated herein and is within the scope of the present disclosure.

Thus, embodiments of the PRESSURE MONITORING TO CONTROL DELIVERY OF THERAPEUTIC AGENT are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system comprising:
    a catheter having a proximal end, a distal region including an opening, a lumen extending from the proximal end to the opening, and a one-way valve, the valve being disposed in proximity to the opening and configured to allow fluid to exit the lumen through the opening;
    an infusion device having a housing, and a reservoir, an infusion mechanism, electronics and a pressure sensor disposed within the housing,
        wherein the reservoir is configured to store therapeutic fluid,
        wherein the infusion mechanism is configured to cause fluid from the reservoir to be infused through the lumen of the catheter when the catheter is operably coupled to the infusion device,
        wherein the pressure sensor is configured and positioned such that the pressure sensor is capable of detecting pressure changes in the lumen of the catheter; the pressure sensor being operably coupled to the electronics,
        wherein the electronics are configured to control the rate that the therapeutic fluid is delivered from the reservoir to the lumen of the catheter and are configured to modify the rate of delivery based on intralumenal pressure detected by the pressure sensor, wherein the rate of delivery is increased if the internal pressure of the catheter is increase, and the rate of delivery is decreased if the internal pressure of the catheter is decreased.

2. A system according to claim 1, wherein the infusion device is an implantable infusion device.

3. A system for delivering a therapeutic fluid to a patient suffering from or at risk of pulmonary arterial hypertension, the system comprising:

a catheter having (i) a proximal end, (ii) a distal delivery region configured to be implanted in a right ventricle or pulmonary artery of a patient, and (iii) a lumen extending from the proximal end to the delivery region, the delivery region comprising a one-way valve configured to allow fluid to flow from the lumen to outside the catheter; and an implantable infusion device operably couplable to the catheter, the infusion device comprising a reservoir for housing the therapeutic fluid, an infusion mechanism for delivering the therapeutic fluid from the reservoir to the catheter, a pressure sensor configured to measure internal pressure of the catheter when the catheter is operably coupled to the infusion device, electronics operably coupled to the pressure sensor and the infusion mechanism, wherein the electronics are configured to compare internal pressure of the catheter at first and second times and are configured to adjust flow rate of fluid delivered to the catheter via the infusion mechanism in response to the measured internal pressure of the catheter, wherein the flow rate is increased if the internal pressure of the catheter is increased and flow rate is decreased if the internal pressure of the catheter is decreased.

\* \* \* \* \*